(12) United States Patent
Uhm et al.

(10) Patent No.: US 10,632,446 B2
(45) Date of Patent: Apr. 28, 2020

(54) ETHYLENE AND ALPHA-OLEFIN POLYMERIZATION APPARATUS AND PREPARATION METHOD

(71) Applicant: DAELIM INDUSTRIAL CO., LTD., Seoul (KR)

(72) Inventors: Jae Hoon Uhm, Daejeon (KR); Jin Hun Ju, Daejeon (KR); Hee Sun Bae, Daejeon (KR); Joo Mi Yeo, Daejeon (KR); Sah Mun Hong, Daejeon (KR)

(73) Assignee: DAELIM INDUSTRIAL CO., LTD., Seoul (KR)

( * ) Notice: Subject to any disclaimer, the term of this patent is extended or adjusted under 35 U.S.C. 154(b) by 0 days.

(21) Appl. No.: 15/109,418

(22) PCT Filed: Jan. 2, 2015

(86) PCT No.: PCT/KR2015/000009
§ 371 (c)(1),
(2) Date: Jun. 30, 2016

(87) PCT Pub. No.: WO2015/102423
PCT Pub. Date: Jul. 9, 2015

(65) Prior Publication Data
US 2016/0325263 A1    Nov. 10, 2016

(30) Foreign Application Priority Data

Jan. 6, 2014    (KR) .................. 10-2014-0001201

(51) Int. Cl.
| | |
|---|---|
| *B01J 19/24* | (2006.01) |
| *C08F 210/16* | (2006.01) |
| *C08F 210/06* | (2006.01) |
| *C08F 10/06* | (2006.01) |
| *B01D 3/06* | (2006.01) |

(Continued)

(52) U.S. Cl.
CPC ............. *B01J 19/24* (2013.01); *B01D 3/06* (2013.01); *B01D 3/143* (2013.01); *C08F 10/06* (2013.01);
(Continued)

(58) Field of Classification Search
CPC ........ B01J 19/00; B01J 19/24; B01J 2219/24; B01D 3/00; B01D 3/06; B01D 3/14;
(Continued)

(56) References Cited

U.S. PATENT DOCUMENTS

| | | | | |
|---|---|---|---|---|
| 3,326,781 | A | * | 6/1967 | Wilson, Jr. ................ C08C 2/06 159/16.3 |
| 3,462,347 | A | * | 8/1969 | Carlson .................... C08J 11/02 203/6 |

(Continued)

FOREIGN PATENT DOCUMENTS

| | | |
|---|---|---|
| EP | 0 186 374 A2 | 7/1986 |
| JP | S57-117595 A | 7/1982 |

(Continued)

OTHER PUBLICATIONS

Office Action dated May 4, 2017 for Chinese Patent Application No. 201580003800.1 and English translation thereof.

(Continued)

*Primary Examiner* — Lessanework Seifu
(74) *Attorney, Agent, or Firm* — Nath, Goldberg & Meyer; Joshua B. Goldberg; Tanya E. Harkins

(57) ABSTRACT

An apparatus and method for economically copolymerizing ethylene and alpha-olefin by reusing reacting raw materials and solvents, comprising: a polymerization reactor where ethylene and alpha-olefin are supplied as reaction raw materials with a solvent, and the reaction raw materials are copolymerized in a solution state to produce a polymerization product comprising a dissolved ethylene and alpha- (Continued)

olefin copolymer; a unit for separating unreacted ethylene, alpha-olefin, low molecular weight oligomer and a polymer, including a flash tower for distilling and separating the unreacted ethylene and alpha-olefin from the polymerization product, and a stripper unit for distilling and separating the solvent and the low molecular weight oligomer having a molecular weight lower than the molecular weight of the ethylene and alpha-olefin copolymer in the polymerization product; and a solvent recovery unit for separating the low molecular weight oligomer from the separated low molecular weight oligomer and solvent to recover the solvent.

5 Claims, 2 Drawing Sheets

(51) Int. Cl.
  *B01D 3/14* (2006.01)
  *C08F 210/02* (2006.01)
(52) U.S. Cl.
  CPC .......... *C08F 210/02* (2013.01); *C08F 210/06* (2013.01); *B01J 2219/24* (2013.01)
(58) Field of Classification Search
  CPC ... B01D 3/143; C08F 2/00; C08F 2/04; C08F 2/06; C08F 10/00; C08F 10/04; C08F 10/06; C08F 210/00; C08F 210/04; C08F 210/06; C08F 210/16; C08F 2/01; C08F 6/04; C08F 6/10; C08F 6/12; C08F 6/28
  See application file for complete search history.

(56) References Cited

U.S. PATENT DOCUMENTS

| | | | |
|---|---|---|---|
| 3,652,515 A | 3/1972 | Love | |
| 3,780,128 A | 12/1973 | Shubkin | |
| 4,271,060 A * | 6/1981 | Hubby | C08F 36/04 524/476 |
| 5,750,816 A † | 5/1998 | Araki | |
| 5,767,331 A | 6/1998 | Oda | |
| 7,799,882 B2 * | 9/2010 | Jiang | C08F 10/00 526/206 |
| 7,888,456 B2 | 2/2011 | Yamamoto | |
| 8,049,052 B2 * | 11/2011 | Kreischer | B01J 31/0237 585/513 |
| 8,071,835 B2 † | 12/2011 | Wu | |
| 8,093,439 B2 † | 1/2012 | Schneider | |
| 2003/0027947 A1 * | 2/2003 | Kobayashi | C07C 2/30 526/70 |

FOREIGN PATENT DOCUMENTS

| | | |
|---|---|---|
| JP | S61-221207 A | 10/1986 |
| JP | H07-121969 B | 12/1995 |
| KR | 10-1989-0002562 B | 7/1989 |
| KR | 10-2009-0068215 A | 6/2009 |
| WO | 2007134837 A1 | 11/2007 |

OTHER PUBLICATIONS

Petrochemical Industry Technology, Issue 3, vol. 18, pp. 58-61, 66(English Abstract), dated Mar. 18, 2011.

Written Opinion of the International Searching Authority dated Apr. 7, 2015 issued in corresponding International Application No. PCT/KR2015/000009.

European search report dated Aug. 11, 2017 for corresponding application No. EP 15733221.4.

Russian search report dated Sep. 27, 2017 for corresponding application No. 2016132466(PCT/KR2015/000009) with English translation attached.

* cited by examiner
† cited by third party

ETHYLENE AND ALPHA-OLEFIN POLYMERIZATION APPARATUS AND PREPARATION METHOD

This is a National Phase Application filed under 35 U.S.C. 371 as a national stage of PCT/KR2015/000009, filed Jan. 2, 2015, an application claiming the benefit of Korean Application No. 10-2014-0001201, filed Jan. 6, 2014, the content of each of which is hereby incorporated by reference in its entirety.

The present invention relates to an apparatus and a method for polymerization of ethylene and alpha-olefin, and more particularly to an apparatus and a method for economically copolymerizing ethylene and alpha-olefin by reusing reacting raw materials and solvents.

BACKGROUND ART

Generally, lubricating oils include base oils and additives for improving the physical properties of the base oils, and the base oils are typically classified to mineral oils and synthetic oils. In general, the mineral oils indicate naphthenic oils which are produced during the separation and purification of crude oils, and the synthetic oils indicate poly-α-olefin (PAO)s which are manufactured by polymerization of α-olefin produced during an oil refining process. In the past, mineral oils had been mainly used as the lubricating base oils, however in recent years, the demand for the synthetic oils having the characteristics of low temperature fluidity, high viscosity index, low volatility at a high temperature, high shear and thermal stability and the like, is increasing. The synthetic oils, compared with the mineral oils, have small viscosity variation according to temperature variation so that excellent lubricity is maintained regardless of seasonal change. Therefore, the synthetic oils have contributed to quietness and fuel efficiency improvement of vehicles, and also, they have some advantages of excellent durability and stability, long lifespan, and being environmentally friendly because of generating less sludge and waste oils. Engine oils using conventional mineral oils do not have sufficient physical and mechanical properties required for the recent engines which are downsized and optimized for high efficiency. Accordingly, the demand for the synthetic oils is increasing in the field of engine oils, gear oils, grease and so on, requiring high quality.

The poly-α-olefins (POAs) used as the synthetic oils are disclosed in U.S. Pat. No. 3,780,128, in which the POAs can be obtained by oligomerization of higher linear α-olefins such as decene-1(C10), dodecene-1(C12) and so on, in the presence of an acid catalyst. However, it has drawbacks that raw materials of higher linear alpha-olefin (LAO) are expensive and supply thereof is not stable. On the other hands, Japanese Unexamined-Publication 1982-117595 discloses a preparing method for synthetic lubricating oils by copolymerizing the ethylene and alpha-olefin, the synthetic lubricating oils having excellent properties in view of viscosity index, oxidation stability, shear stability, heat resistance etc. In the copolymerization of ethylene and alpha-olefin, is used a catalyst composition composed by titanium compound and organic aluminum compound. The titanium compound catalyst has large catalytic activity, but molecular weight of the copolymer obtained has wide distribution and low regularity. Accordingly, it is difficult to obtain products having high flash points which are useful for lubricating oils, lubricating oil additives, fuel oil additives etc., and in case of high viscosity products, cost thereof is high so that it is not practical. Also, U.S. Pat. No. 5,767,331 discloses a method for copolymerizing the ethylene and alpha-olefin, specifically copolymerizing ethylene and propylene, by using vanadium-based catalyst composition containing vanadium compound and organic aluminum compound. The copolymer prepared by using vanadium-based catalyst composition has narrow molecular weight distribution and superior uniformity. But the copolymer prepared by using vanadium-based catalyst composition generally has very low polymerization activity, and accompanies large amount of catalyst sludge so that it has a drawback of requiring the additional de-catalytic process, which is common problem on the 1st generation catalyst such as Ziegler-Natta catalyst. In addition, Japanese Unexamined-Publication S61-221207, Japanese Unexamined-Publication H7-121969 etc. disclose a method for preparing the copolymer with high polymerization activity by using a catalyst system composed by metallocene compound such as zirconocene and so on and organoaluminum oxy-compound, and Japanese Patent 2796376 discloses a method for preparing synthetic lubricating oils by copolymerizing the ethylene and alpha-olefin, by using a catalyst system composed by specific metallocene catalyst and organoaluminum oxy-compound.

DISCLOSURE

Technical Problem

Therefore, it is an object of the present invention to provide an apparatus and a method for efficiently copolymerizing ethylene and alpha-olefin, specifically propylene, which is smoothly supplied and is cheap.

It is another object of the present invention to provide an apparatus and a method for economically copolymerizing ethylene and alpha-olefin by reusing reacting raw materials and solvents.

It is still another object of the present invention to provide an apparatus and a method for preparing copolymer of ethylene and alpha-olefin, which can be used as synthetic oils of high-quality and high-performance.

Technical Solution

In an embodiment for achieving the objects, the present invention provides an apparatus for polymerizing ethylene and alpha-olefin, comprising: a polymerization reactor, to which ethylene and alpha-olefin of reacting raw materials and solvents are fed and in which the reacting raw materials are polymerized in solution state, for producing a polymerization product of ethylene and alpha-olefin copolymer which is dissolved in the solvent; a separation section including a flash tower for separating unreacted ethylene and alpha-olefin contained in the polymerization product by distilling; and a stripper for separating low molecular weight oligomers having lower molecular weight than the ethylene and alpha-olefin copolymer contained in the polymerization product, by distilling; and a solvent recovery section for separating the low molecular weight oligomers from the solvents and low molecular weight oligomers which are separated and then for recovering the solvents.

In an embodiment for achieving the objects, the present invention provides a method for polymerizing ethylene and alpha-olefin, comprising the steps of: copolymerizing ethylene and alpha-olefin of reaction raw materials in presence of solvents, to produce a polymerization product in which low molecular weight compounds containing unreacted ethylene and alpha-olefin, the solvents, ethylene and alpha-olefin copolymers and ethylene and alpha-olefin oligomers; separating the unreacted ethylene and alpha-olefin contained in the polymerization product by distilling; separating the solvents and the low molecular weight compounds having lower molecular weight than the ethylene and alpha-olefin copolymer and contained in the polymerization product by distilling, to obtain pure polymerization product; and separating the low molecular weight oligomers from the solvents and the low molecular weight compounds previously separated by distilling to recover the solvents, and then reusing the recovered solvents as solvents for polymerization.

Technical Effects

In the apparatus and method for polymerizing, ethylene and alpha-olefin of reacting raw materials, specifically lower alpha-olefin such as propylene etc., which are smoothly supplied and cheap, are efficiently copolymerized so that as well as synthetic oils having high quality and high performance can be prepared, it is economical since the reacting raw materials and solvents can be reused.

EXAMPLES

Hereinafter, the present invention will be described in detail with reference to the accompanying drawings.

Figure 1:
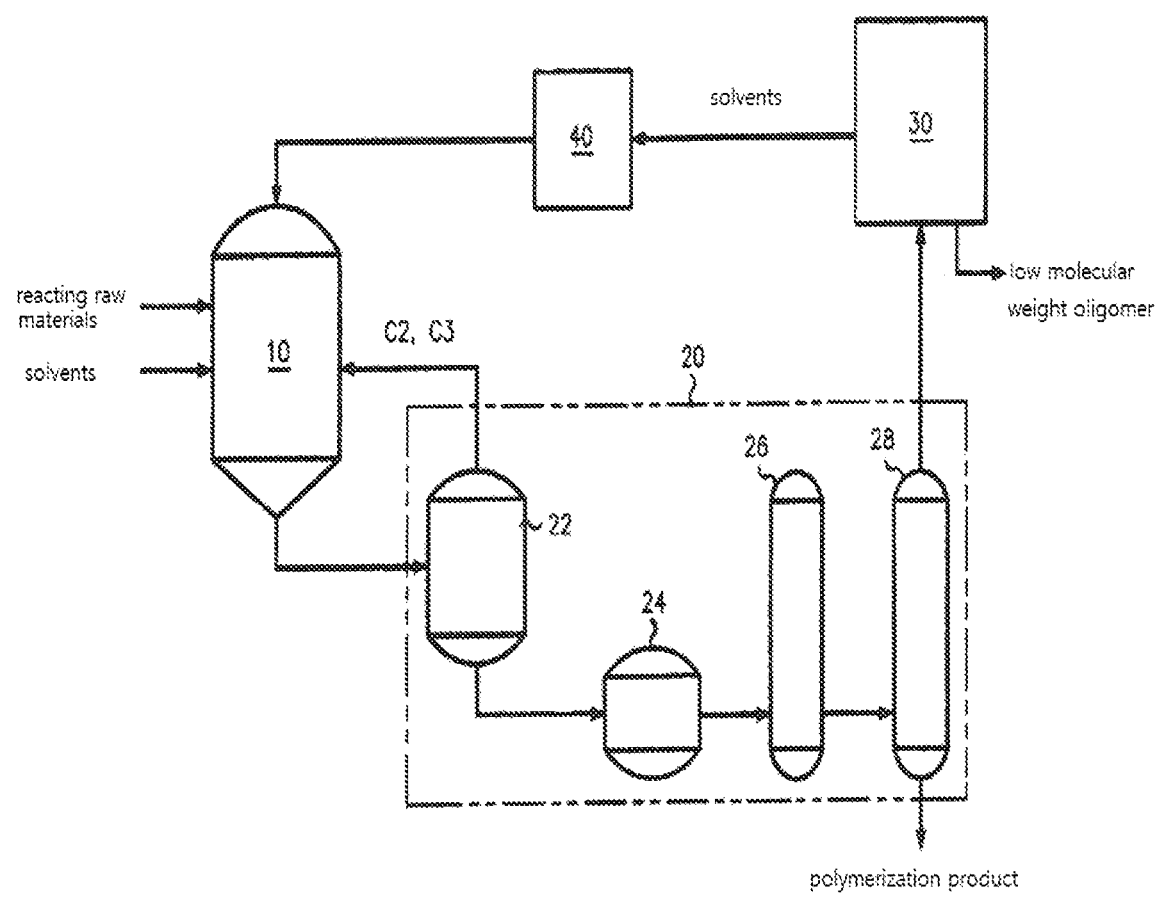
FIG. 1 is a schematic diagram illustrating an apparatus for polymerizing ethylene and alpha-olefin according to an embodiment of the present invention.

FIG. 1 is a block diagram illustrating overall configuration of an apparatus for polymerizing ethylene and alpha-olefin according to an embodiment of the present invention. As shown in FIG. 1, the apparatus for polymerizing ethylene and alpha-olefin according to the present invention comprises a polymerization reactor (10), a separation section (20) for separating unreacted ethylene and alpha-olefin, low molecular weight oligomer and polymerization product, and a solvent recovery section (30), and if needed, further comprises a solvent purification section (40).

Ethylene and alpha-olefin, as the reacting raw materials, and solvents are fed to the polymerization reactor (10), and in the polymerization reactor the reacting raw materials are copolymerized in a solution state to produce the polymerization product containing ethylene-and-alpha-olefin copolymer dissolved in the solvent. Conventional additives for controlling the polymerization reaction, such as a catalyst, a molecular weight modifier and so on, may be further supplied to the polymerization reactor (10) together with the reacting raw materials and the solvent. The polymerization reaction can be carried out in a batch mode, a semi-continuous mode or continuous mode, preferably in a continuous mode using a continuous stirred tank reactor (Continuous Stirred Tank Reactor, CSTR). The CSTR increases the mixing effect of the reacting materials and the catalyst during the retention time at the reactor, makes uniform mixture and maintains temperature of the reaction system through a heat exchange. The effluent (polymerization product) produced from the polymerization reactor (10) includes low molecular weight compounds containing unreacted ethylene, alpha-olefin and so on, solvents, copolymers of ethylene and alpha-olefin (pure polymerization product), and low molecular weight oligomers of ethylene and alpha-olefin.

The separation section (20) is for devolatilizing volatile components contained in the polymerization product and for separating the polymerization product of ethylene and alpha-olefin copolymer, in the present invention, the separation section (20) includes a flash tower (22), a washing unit (24), a first stripper (26) and a second stripper (28). The flash tower (22) separates with flash distillation, first low molecular weight compounds contained in the effluent, specifically compounds having lower molecular weights than the solvents, for example unreacted ethylene and alpha-olefin having carbon atoms of 2 to 5, preferably 2 to 3. In detail, when the effluent containing the pure polymerization product is supplied to the flash tower (22) in which the atmospheric pressure or less and temperature of 50 to 150° C. are maintained, the solvents, the oligomers and the copolymers remain in liquid state, and the lightest first low molecular weight compounds are flashed in gaseous state, so that the first low molecular weight compounds are separated by simple distillation. The pressure and the temperature of the flash tower (22) are set for the materials having molecular weights lower than the reaction raw materials of ethylene and alpha-olefin and the solvents to be vaporized, and for the materials having molecular weights higher than the solvent to be remaining in liquid state. The first low molecular weight compound is obtained from a top the flash tower (22), and the solvents and the polymerization products are obtained from a bottom of the flash tower (22). The first low molecular weight compounds separated from the flash tower (22) can be reused as reaction raw materials after a condensation/purification process.

If necessary, a washing unit (24) for inactivating the catalyst contained in the polymerization product after completing the polymerization can be further installed at a rear end of the flash tower (22), specifically between the flash tower (22) and the strippers (26, 28). The catalyst can be contained in the polymerization product, so that there is needs to prevent an additional reaction after the polymerization by adding to the polymerization product a catalyst kill for suppressing the catalyst activity. As an example of the catalyst kill, aqueous sodium hydroxide solution (caustic solution, 20 wt % NaOH solution) can be used. The washing unit (24) can be a mixer such as a washing drum which can contact the polymerization product with the catalyst kill. For example, the polymerization product and the caustic aqueous solution are put in the washing drum and mixed with stirring so that the catalyst in the polymerization product can be inactivated. Here, the catalyst inactivated by the caustic aqueous solution exists in a dissolved state in the aqueous solution layer. Therefore, the aqueous solution layer containing the catalyst can be separated from the organic layer in which the polymerization product is dissolved, through a specific gravity difference by using a separation drum etc., and the catalyst component can be removed from the polymerization product. That is, the organic layer including the polymerization product and the solvent can be obtained from a top of the separation drum and the aqueous solution layer including the inactivated catalyst and the caustic solution can be obtained from a bottom of the separation drum.

The stripper (26, 28) is a distillation column for separating the solvents and the second low molecular weight compound including low molecular weight oligomer (Light polymer) contained in the effluent by distillation. Since excessive amount of solvents is contained in effluent, it is preferable to use a vacuum stripper, in which so as to minimize the entrainment of the polymerization product, the solvent and the low molecular weight oligomer at the top are refluxed and the second low molecular weight compounds are removed from the top of the distillation column. Accordingly, the temperature and the pressure of the stripper (26, 28) is set to distil the solvents and the low molecular weight oligomers (oligomers of ethylene and alpha-olefin), wherein the low molecular weight oligomers have molecular weight lower than the polymerization product of ethylene-and-alpha olefin copolymer. The weight-average molecular weight of the low molecular weight oligomers is 400 or less, preferably 350 or less, more preferably 300 or less, most preferably a range of molecular weight of used solvents through 250. Accordingly, the stripper (26, 28) distils and separates the low molecular weight oligomers having molecular weight of 400 or less, preferably 350 or less, more preferably 300 or less, most preferably 250 or less. It is preferable that the stripper (26, 28) is constituted by a first stripper (26) and a second stripper (28). The first stripper (26) is operated in pressure of 20~30 Torr and temperature of 80~100° C. so as to primarily separate the solvents and the second molecular weight compounds of low molecular weight oligomers etc., and the second stripper (28) is operated in pressure of 1~10 Torr (high vacuum) and temperature of 220~240° C. so as to secondarily separate the second molecular weight compounds remaining in the polymerization product, finally thereby producing pure copolymer (polymerization product). As the amount of the low molecular weight oligomers in the polymerization product increases, the flash point of the polymerization product is lowered. Therefore, it is desirable to minimize the remaining amount of the oligomers in the polymerization product by sequentially removing the low molecular weight oligomers while increasing the temperature and degree of vacuum of the stripper (26, 28). At this time, as needed, nitrogen ($N_2$) can be further injected to the polymerization product ($N_2$ Stripping) to lower the partial pressure of the low molecular weight compounds (Light polymer) and to reduce the remaining amount of the low molecular weight oligomers. In addition, the moisture contained in the solvent can be separated and removed by a side-cut (extracting necessary component at one stage of the distillation column) at a stripper condenser positioned on the top of the distillation column of the stripper (26, 28).

The solvent recovery section (30) is constituted by a distillation column for separating the low molecular weight oligomers from the low molecular weight oligomers and the solvents which are separated from the effluent, and recovering high-purity solvents. The stage number of the distillation column composing the solvent recovery section (30) is for example 20 to 50, and the high-purity solvents can be obtained at the top of the distillation column. To minimize the amount of the oligomers in the solvents, the temperature and pressure of the distillation column should be set appropriately so as to separate the solvents and the oligomers, and it is preferable to distil the solvents with high reflux ratio. The recovered solvent can be reused as solvents for polymerization. The solvent purification section (40) removes impurities from the solvents free of the polymerization products and the low molecular weight oligomers, which can be installed as needed.

Figure 2:
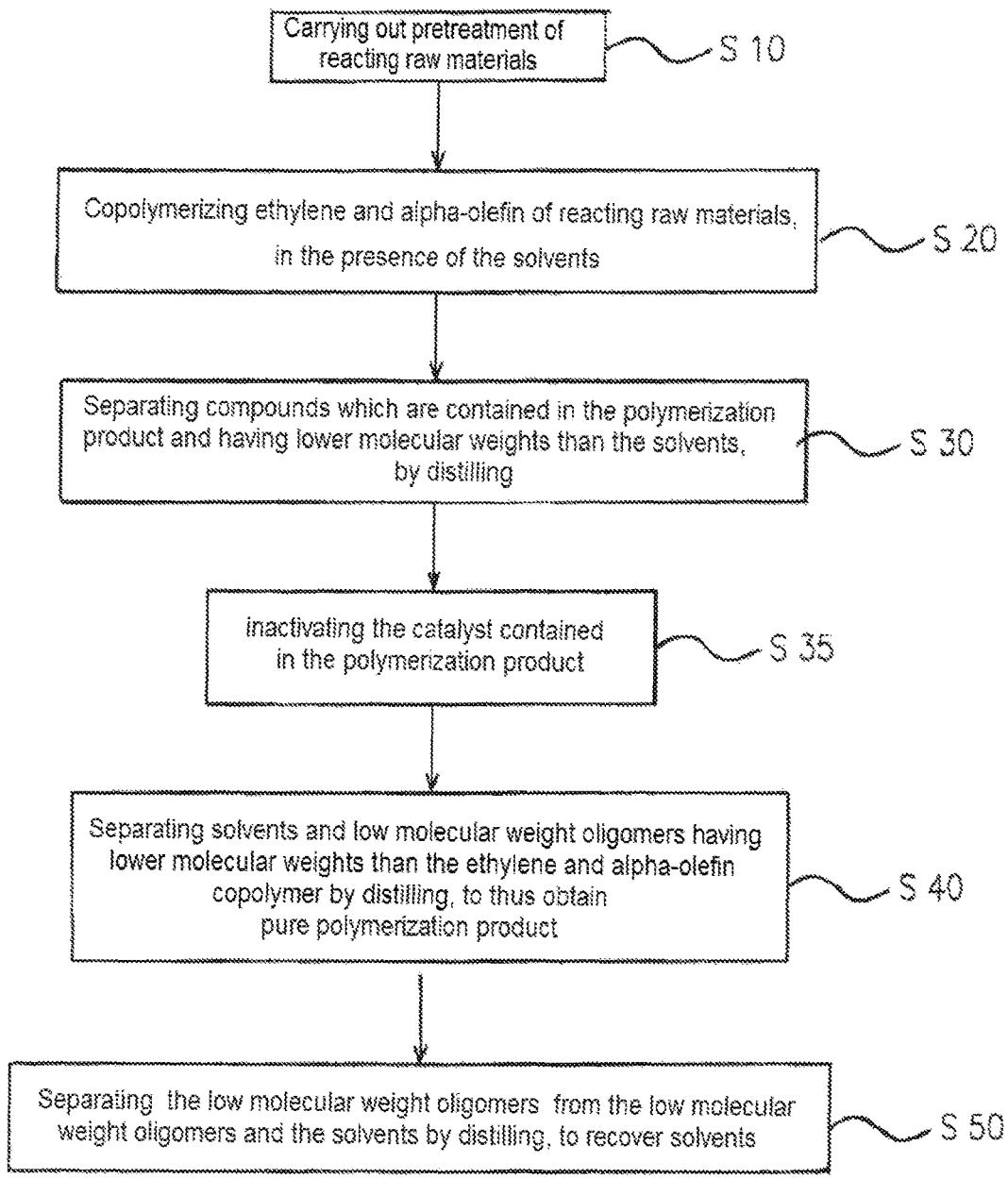
FIG. 2 is a flow chart illustrating a method for polymerizing ethylene and alpha-olefin according to an embodiment of the present invention.

FIG. 2 is a flow chart illustrating a method for polymerizing ethylene and alpha-olefin according to an embodiment of the present invention. As shown in FIG. 2, in the polymerization method of ethylene and alpha-olefin according to the present invention, it is preferable to carry out a pretreatment (S10) for, from the reacting raw materials, removing materials (poison, impurity) which may reduce the catalyst activity, such as moisture, oxygen ($O_2$), $CO_2$, sulfur, and so on. For example, if the reacting raw materials pass through the column constituted by a scavenger for removing oxygen ($O_2$) and sulfur (for example, Ridox™ Oxygen Scavenger, manufacturer: Fisher Chemical), alumina for removing CO and $CO_2$, molecular sieve for removing moistures, and so on, materials which reduce the catalyst activity can be removed from the reacting raw materials. Next, ethylene and alpha-olefin, the reacting raw materials, are copolymerized in the presence of the solvents (S 20). The effluents resulted from the copolymerization include low molecular weight compounds containing the unreacted ethylene, alpha-olefin, solvents, copolymers of ethylene and alpha-olefin, oligomers of ethylene and alpha-olefin and so on. Next, the first low molecular weight compounds which are contained in the effluents and having lower molecular weights than the solvents (for example unreacted ethylene, alpha-olefin) are separated by distilling (S 30). Subsequently, solvents and low molecular weight oligomers contained in the effluents and having lower molecular weights than the ethylene and alpha-olefin copolymer (second molecular weight compounds) are separated by distilling, to thus obtain pure polymerization product (S 40). At this time, if necessary, a catalyst washing process (S 35) for inactivating the catalyst contained in the polymerization product can be further carried out after separating the first low molecular weight compounds (S 30). Finally, the low molecular weight oligomers are separated from the low molecular weight oligomers and the solvents by distilling, to recover high purity solvents, and thus the obtained solvents can be reused as solvents for further polymerization (S50).

The reacting raw materials used for the polymerization reaction of the present invention are ethylene and alpha-olefin having 3 to 20 carbon atoms. As alpha-olefin having 3 to 20 carbon atoms, straight-chain alpha-olefins, branched-chain alpha-olefins and mixtures thereof can be used alone or in combination, wherein the straight-chain alpha-olefins includes propylene, 1-butene, 1-pentene, 1-hexene, etc., and the branched-chain alpha-olefins includes isobutylene, 3-methyl-1-butene, 4-methyl-1-pentene, etc. Lower linear alpha-olefin having 3 to 5 carbon atoms is preferable, and propylene is more preferable. The polymerization reaction can be carried out by using inert solvents such as propane, butane, pentane, hexane as a medium, Preferably, solvents having higher molecular weight than alpha-olefin used for the polymerization can be used, preferably saturated hydrocarbon compounds having 4 to 8 carbon atoms, more preferably hexane having 6 carbon atoms. For example, the carbon atom number of the solvents is greater than that of the alpha olefins used for the polymerization reaction, by 1 or more. The reacting raw materials used in the present invention have relatively high vapor pressure compared to the solvents, therefore it is easy to recover unreacted raw materials. For example, when the reacting raw materials are ethylene and propylene, the unreacted raw materials can be recovered at atmospheric pressure and temperature of 0 to 100° C. preferably 0 to 50° C. Also, in addition, advantageously, the reacting raw materials used in the present invention are stably supplied and demanded, and inexpensive, compared with higher alkene such as decene-1, etc.

In the polymerization reaction according to the present invention, as a catalyst, metallocene catalyst is preferable rather than using the first generation of Ziegler-Natta catalyst etc. If needed, single site catalyst system can be used by mixing a catalyst and a cocatalyst such as organoaluminum oxy-compound organoaluminum compounds, borate, aluminoxane etc. On the other hand, as the molecular weight modifier, hydrogen ($H_2$) can be used. In the copolymerization of ethylene and alpha-olefin according to the invention, the polymerization temperature varies depending on the reaction materials, the reaction condition and so on, however, generally the polymerization temperature is from 80 to 150° C., preferably from 90 to 120° C. The polymerization pressure is from 10 to 50 bars, preferably 20 to 40 bars, more preferably from 25 to 35 bars. Here, when the polymerization temperature is too low, copolymer having high molecular weight is likely to be formed excessively. When the polymerization temperature is too high, there is a possibility that the catalyst activity is reduced due to the thermal stability. The copolymerization condition of the ethylene and alpha-olefin was disclosed in detail in Korean Patent Application No. 10-2012-0130792 (filing date: Nov. 19, 2012) belong to the present applicant, and all the contents thereof is herein incorporated.

The copolymer of the present invention which is formed by the polymerization of ethylene and alpha-olefin having 3 to 20 carbon atoms, is a random copolymer being liquid at room temperature, wherein the alpha-olefin units are uniformly distributed in chains of the copolymer. The copolymer includes ethylene unit of 40 to 60 mol %, preferably 45 to 55 mol % and unit of alpha-olefin having 3 to 20 carbon atoms of 40 to 60 mol %, preferably 45 to 55 mol %, wherein the ethylene unit is derived from ethylene and the unit of alpha-olefin having 3 to 20 carbon atoms is derived from alpha-olefin having 3 to 20 carbon atoms. In the copolymer of the present invention, when the amount of ethylene unit is less than 40 mol %, the amount of propylene etc. is increased so that the liquid copolymer may not be formed. When the amount of ethylene unit is more than 60 mol %, the amount of ethylene is excessively increased so that it is difficult to form liquid copolymers or the copolymers cannot be suitable as synthetic lubricating oils. The number-average molecular weight (Mn) of the present copolymer is 500 to 10,000, preferably 800 to 6,000 and its molecular weight distribution (Mw/Mn, Mw is the weight-average molecular weight) is 3 or less, preferably 2 or less. The number-average molecular weight (Mn) and the molecular-weight distribution (Mw/Mn) are measured with gel permeation chromatography (GPC). The liquid copolymer of ethylene and alpha-olefin according to the present invention has monomers distributed evenly over the entire length of the copolymer molecules, narrow distribution of the composition and molecular weight, excellent uniformity, small distribution of the double bond, highly activity and less sludge so that it is particularly useful as synthetic oils for requiring high viscosity index, low-temperature viscosity characteristics, shear and thermal stability, durability, etc.

The synthetic oils made of copolymers of ethylene and the alpha-olefin according to the present invention can be used as lubricant base oils, viscosity modifiers, viscosity index improvers, lubricity additives etc. in the fields of automotive lubricants, gear oils, industrial lubricating oils, greases.

The invention claimed is:

1. An apparatus for polymerizing ethylene and alpha-olefin, comprising:
a quantity of reacting raw materials and solvents, wherein the quantity of reacting raw materials and solvents comprises ethylene and alpha-olefin;
a polymerization reactor, to which the ethylene and alpha-olefin are fed in and in which the reacting raw materials are polymerized in solution state, for producing a polymerization product of ethylene and alpha-olefin copolymer which is dissolved in the solvent;
a separation section including a flash tower for separating an unreacted portion of the ethylene and the alpha-olefin contained in the polymerization product by distillation, the flash tower vaporizing the unreacted portion of the ethylene and the alpha-olefin to separate gaseous unreacted ethylene and alpha-olefin from the polymerization product, a remaining portion of the polymerization product including the ethylene and alpha-olefin copolymer in a liquid mixture of the solvent and low molecular weight oligomers having a lower molecular weight than the ethylene and alpha-olefin copolymer, the separation section further including a stripper for separating the ethylene and alpha-olefin copolymer from the liquid mixture of the solvent and the low molecular weight oligomers by distillation; and
a solvent recovery section for separating the low molecular weight oligomers from the solvents and low molecular weight oligomers which are separated and then for recovering the solvents,
wherein the alpha-olefin is linear alpha-olefin having 3 to 5 carbon atoms and the solvents are saturated hydrocarbon compounds having 4 to 8 carbon atoms,
wherein the solvents have a molecular weight higher than the molecular weight of the alpha-olefin,
wherein the ethylene and alpha-olefin copolymer is a random copolymer with an average molecular weight between 500 and 10,000, the ethylene and alpha-olefin copolymer being in a liquid state at room temperature, and
wherein a washing unit is provided between the flash tower and the stripper for inactivating a catalyst contained in the polymerization product, and a stripper condenser is provided on a top of a distillation column of the stripper to separate and remove moisture contained in the solvents.

2. The apparatus of claim 1, wherein the flash tower separates the unreacted ethylene and alpha-olefin contained in the polymerization product by flash-distilling.

3. The apparatus of claim 1, wherein the washing unit between the flash tower and the stripper, inactivates the catalyst contained in the polymerization product under the completion of polymerization.

4. The apparatus of claim 1, wherein the stripper is constituted by a first stripper and a second stripper, and wherein the first stripper is operated in a pressure of 20 to 30 Torr and temperature of 80 to 100° C. so as to primarily separating the solvents and the low molecular weight oligomers, and the second stripper is operated in a pressure of 1 to 10 Torr and a temperature of 220 to 240° C. so as to secondarily separating the solvents and the low molecular weight oligomers remaining in the polymerization product.

5. The apparatus of claim 1, wherein the pressure and the temperature of the flash tower are set so as to distil the reaction raw materials of ethylene and alpha-olefin and materials having molecular weight below the reaction raw materials, and then to remain the solvent.

* * * * *